(12) United States Patent
Wagner et al.

(10) Patent No.: US 8,314,054 B2
(45) Date of Patent: *Nov. 20, 2012

(54) MILD MULTI-PHASED PERSONAL CARE COMPOSITION

(75) Inventors: Julie Ann Wagner, Cincinnati, OH (US); Karl Shiqing Wei, Mason, OH (US); Edward Dewey Smith, III, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/066,642

(22) Filed: Feb. 25, 2005

(65) Prior Publication Data

US 2005/0192187 A1 Sep. 1, 2005

Related U.S. Application Data

(60) Provisional application No. 60/548,739, filed on Feb. 27, 2004.

(51) Int. Cl.
*A61K 7/50* (2006.01)

(52) U.S. Cl. ........ 510/130; 510/510; 510/424; 510/426; 510/463

(58) Field of Classification Search .................. None
See application file for complete search history.

(56) References Cited

U.S. PATENT DOCUMENTS

| | | |
|---|---|---|
| 2,020,454 A | 11/1935 | Bisbee et al. |
| 2,658,072 A | 11/1953 | Kosmin |
| 2,986,271 A | 5/1961 | Forrer |
| 3,455,440 A | 7/1969 | West |
| 3,479,429 A | 11/1969 | Morshauser et al. |
| 3,533,955 A | 10/1970 | Pader et al. |
| 3,542,256 A | 11/1970 | Waterman |
| 3,618,757 A | 11/1971 | Funkhouser |
| 3,800,998 A | 4/1974 | Gask |
| 3,850,365 A | 11/1974 | Dietrich |
| 3,899,076 A | 8/1975 | Florian |
| 3,929,678 A | 12/1975 | Laughlin et al. |
| 3,937,811 A | 2/1976 | Papantoniou et al. |
| 3,951,679 A | 4/1976 | Bernhard et al. |
| 3,980,767 A | 9/1976 | Chown et al. |
| 4,159,028 A | 6/1979 | Barker et al. |
| 4,263,363 A | 4/1981 | Buck et al. |
| 4,335,103 A | 6/1982 | Baker et al. |
| 4,379,753 A | 4/1983 | Bolich, Jr. |
| 4,425,322 A | 1/1984 | Harvey et al. |
| 4,518,578 A | 5/1985 | Hayes et al. |
| D292,879 S | 11/1987 | Smith |
| 4,818,575 A | 4/1989 | Hirata et al. |
| 4,966,205 A | 10/1990 | Tanaka |
| 4,980,155 A | 12/1990 | Shah et al. |
| 5,002,680 A | 3/1991 | Schmidt et al. |
| 5,059,414 A | 10/1991 | Dallal et al. |
| 5,223,315 A | 6/1993 | Katsura et al. |
| 5,228,912 A | 7/1993 | Herget et al. |
| 5,304,334 A | 4/1994 | Lahanas et al. |
| 5,393,450 A | 2/1995 | Shana'a et al. |
| 5,455,035 A | 10/1995 | Guerrero et al. |
| 5,487,168 A | 1/1996 | Geiner et al. |
| 5,540,853 A | 7/1996 | Trinh et al. |
| 5,556,628 A | 9/1996 | Derian et al. |
| 5,578,299 A | 11/1996 | Starch |
| 5,612,307 A | 3/1997 | Chambers et al. |
| 5,632,420 A | 5/1997 | Lohrman et al. |
| 5,635,171 A | 6/1997 | Nadaud |
| 5,661,189 A | 8/1997 | Grievson et al. |
| 5,687,779 A | 11/1997 | Andersson et al. |
| 5,716,920 A | 2/1998 | Glenn et al. |
| 5,851,978 A | 12/1998 | Shana'a |
| 5,873,494 A | 2/1999 | Dallas, Jr. |
| 5,914,117 A | 6/1999 | Lavaud |
| 5,925,603 A | 7/1999 | D'Angelo |
| 5,929,019 A | 7/1999 | Puvvada et al. |
| 5,947,335 A | 9/1999 | Milio et al. |
| 5,952,286 A * | 9/1999 | Puvvada et al. ............... 510/417 |
| 5,954,213 A | 9/1999 | Gerhart et al. |
| 5,965,500 A | 10/1999 | Puvvada |
| 5,965,501 A | 10/1999 | Rattinger et al. |
| 5,972,361 A | 10/1999 | Fowler et al. |
| D426,158 S | 6/2000 | Flurer et al. |
| 6,150,312 A | 11/2000 | Puvvada et al. |
| 6,153,177 A | 11/2000 | Bartolone et al. |
| 6,174,845 B1 | 1/2001 | Rattinger et al. |
| 6,176,391 B1 | 1/2001 | Rehkemper et al. |
| 6,176,395 B1 | 1/2001 | Abbott et al. |
| 6,190,648 B1 | 2/2001 | Kouzu et al. |
| 6,194,364 B1 * | 2/2001 | Glenn, Jr. ...................... 510/130 |
| D438,460 S | 3/2001 | Hammond |

(Continued)

FOREIGN PATENT DOCUMENTS

CA 2246316 6/1998
(Continued)

OTHER PUBLICATIONS

XP 002332778 "Dove All Day Moisturizing Body Wash" Online URL: http://www.ewg.org/reprots/skindeep/productinfo.php?prod_id=901910.
XP002332779 "Olay Daily Renewal Moisturizing Body Wash" Online URL: http://householdprdoucts.nlm.nih.gov/cgi-bin/household.brands?tbl=brands&id=16003084.
C.D. Vaughan, "Solubility, Effects in Product, in Package, Penetration and Preservation," Cosmetic and Toiletries, vol. 103, Oct. 1988.
Crank, Mathematics of Diffusion, 2nd Edition, nma 1975, p. 63.
CTFA International Cosmetic Ingredient Dictionary, Fourth Edition, Aug. 12, 1991, pp. 12 and 80.
Household Products Database, Brand Information, "Olay Daily Renewal Moisturizing Body Wash, Calming, "[Online] URL: http://householdproducts.nlm.nih.gov/cgi-bin/household/brands?tbl=brands&id=16003084, accessed Feb. 8, 2006 (2 pages).
Milton, Introduction to Probability and Statistics, $4^{th}$ Edition (Section 9.2: Testing Hypotheses on a Proportion), pp. 129-131, accessed Jun. 9, 2008.
J. Caelles et al., "Anionic and Cationic Compounds in Mixed Systems," Cosmetics & Toiletries, vol. 106, Apr. 1991. pp. 49-54.

(Continued)

*Primary Examiner* — Necholus Ogden, Jr.

(57) ABSTRACT

The present invention relates to a mild multi-phased personal care composition that contains a surfactant component containing a surfactant or a mixture of surfactants; where said mild multi-phased personal care composition has a Structured Domain Volume Ratio of at least about 45%.

29 Claims, No Drawings

U.S. PATENT DOCUMENTS

| | | | |
|---|---|---|---|
| D439,165 S | 3/2001 | Erckelbout et al. |
| 6,213,166 B1 | 4/2001 | Thibiant et al. |
| D441,645 S | 5/2001 | Longhurst |
| 6,232,496 B1 | 5/2001 | Carr et al. |
| 6,245,323 B1 | 6/2001 | Christie et al. |
| 6,245,344 B1 | 6/2001 | Thibiant et al. |
| 6,268,322 B1 | 7/2001 | St. Lewis et al. |
| 6,306,806 B1 | 10/2001 | St. Lewis et al. |
| 6,335,312 B1 | 1/2002 | Coffindaffer et al. |
| 6,340,723 B1 | 1/2002 | Nita et al. |
| D455,655 S | 4/2002 | Bunce |
| 6,367,519 B2 | 4/2002 | Thibiant et al. |
| 6,383,999 B1 | 5/2002 | Coyle et al. |
| 6,385,992 B1 | 5/2002 | Flore, Jr. |
| 6,394,323 B2 | 5/2002 | McClean et al. |
| 6,419,783 B1 | 7/2002 | Rainey et al. |
| 6,426,326 B1* | 7/2002 | Mitra et al. ............... 510/130 |
| 6,429,177 B1* | 8/2002 | Williams et al. ............ 510/130 |
| 6,495,498 B2 | 12/2002 | Niemiec et al. |
| 6,506,391 B1 | 1/2003 | Biatry |
| 6,517,939 B1 | 2/2003 | Moini et al. |
| 6,521,216 B1 | 2/2003 | Glandorf et al. |
| 6,534,456 B2* | 3/2003 | Hayward et al. ............ 510/130 |
| 6,534,457 B2* | 3/2003 | Mitra ........................ 510/130 |
| 6,547,063 B1 | 4/2003 | Zaveri et al. |
| 6,555,509 B2 | 4/2003 | Abbas et al. |
| 6,564,978 B1 | 5/2003 | Safian et al. |
| 6,574,985 B2 | 6/2003 | Fiore, Jr. |
| 6,589,509 B2 | 7/2003 | Keller et al. |
| 6,652,134 B2 | 11/2003 | Lloyd |
| 6,663,855 B2 | 12/2003 | Frechet et al. |
| 6,664,217 B1 | 12/2003 | Puvvada et al. |
| 6,673,371 B2 | 1/2004 | Brown et al. |
| 6,673,755 B2 | 1/2004 | Wei et al. |
| D486,395 S | 2/2004 | Lovell et al. |
| D486,398 S | 2/2004 | Lovell et al. |
| 6,691,394 B1 | 2/2004 | McClean |
| 6,695,510 B1 | 2/2004 | Look et al. |
| 6,782,307 B2 | 8/2004 | Wilmott et al. |
| 6,919,303 B2 | 7/2005 | Pham et al. |
| 6,924,256 B2 | 8/2005 | Massaro et al. |
| 7,143,893 B2 | 12/2006 | Kelly |
| 7,144,542 B2 | 12/2006 | Holzer et al. |
| 7,273,837 B2 | 9/2007 | Boutique et al. |
| 7,511,003 B2 | 3/2009 | Focht et al. |
| 7,524,807 B2 | 4/2009 | Clapp et al. |
| 7,666,825 B2 | 2/2010 | Wagner et al. |
| 8,088,721 B2 | 1/2012 | Soffin et al. |
| 8,105,996 B2 | 1/2012 | Wei et al. |
| 2001/0036467 A1 | 11/2001 | Thibiant et al. |
| 2002/0004468 A1 | 1/2002 | Hodge et al. |
| 2002/0010110 A1 | 1/2002 | Hayward et al. |
| 2002/0022040 A1 | 2/2002 | Robinson et al. |
| 2002/0173436 A1 | 11/2002 | Sonnenberg et al. |
| 2003/0003069 A1 | 1/2003 | Carson et al. |
| 2003/0152540 A1 | 8/2003 | Putman et al. |
| 2003/0161852 A1 | 8/2003 | Miller et al. |
| 2003/0180246 A1* | 9/2003 | Frantz et al. .............. 424/70.21 |
| 2003/0222100 A1 | 12/2003 | Husband et al. |
| 2004/0048757 A1 | 3/2004 | Zhang et al. |
| 2004/0048758 A1 | 3/2004 | Zhang et al. |
| 2004/0057920 A1 | 3/2004 | Focht et al. |
| 2004/0091445 A1 | 5/2004 | Dykstra et al. |
| 2004/0092415 A1* | 5/2004 | Focht et al. ................ 510/130 |
| 2004/0105827 A1 | 6/2004 | Grimm et al. |
| 2004/0146475 A1 | 7/2004 | Peffly et al. |
| 2004/0158940 A1 | 8/2004 | Wells et al. |
| 2004/0180020 A1 | 9/2004 | Manelski et al. |
| 2004/0219119 A1 | 11/2004 | Wei et al. |
| 2004/0223929 A1 | 11/2004 | Clapp et al. |
| 2004/0223991 A1 | 11/2004 | Clapp et al. |
| 2004/0223992 A1 | 11/2004 | Clapp et al. |
| 2004/0232023 A1 | 11/2004 | Bansal et al. |
| 2004/0235693 A1 | 11/2004 | Wei et al. |
| 2004/0242706 A1 | 12/2004 | Wiersema et al. |
| 2004/0248748 A1 | 12/2004 | Wei et al. |
| 2004/0248749 A1 | 12/2004 | Mitra et al. |
| 2005/0003975 A1 | 1/2005 | Browne et al. |
| 2005/0020468 A1 | 1/2005 | Frantz et al. |
| 2005/0100570 A1 | 5/2005 | Wei et al. |
| 2005/0139574 A1 | 6/2005 | Simone et al. |
| 2005/0143269 A1 | 6/2005 | Wei et al. |
| 2005/0192187 A1 | 9/2005 | Wagner et al. |
| 2005/0192188 A1 | 9/2005 | Wagner et al. |
| 2005/0192189 A1 | 9/2005 | Wagner et al. |
| 2005/0238680 A1 | 10/2005 | Stella et al. |
| 2005/0249758 A1 | 11/2005 | Di Puccio Pagano |
| 2005/0269372 A1 | 12/2005 | Smith |
| 2005/0276768 A1 | 12/2005 | Wei et al. |
| 2006/0002880 A1 | 1/2006 | Peffly et al. |
| 2006/0008438 A1 | 1/2006 | Velarde et al. |
| 2006/0079419 A1 | 4/2006 | Wagner et al. |
| 2006/0079420 A1 | 4/2006 | Wagner et al. |
| 2006/0094628 A1 | 5/2006 | Wei et al. |
| 2006/0210505 A1 | 9/2006 | Clapp et al. |
| 2006/0276357 A1 | 12/2006 | Smith, III et al. |
| 2007/0081953 A1 | 4/2007 | Dahms et al. |
| 2007/0105746 A1 | 5/2007 | Dahms et al. |
| 2007/0141001 A1 | 6/2007 | Clapp et al. |
| 2007/0187274 A1 | 8/2007 | Dalea et al. |
| 2007/0248562 A1 | 10/2007 | Berry et al. |
| 2007/0280976 A1 | 12/2007 | Taylor et al. |
| 2010/0209374 A1 | 8/2010 | Wei et al. |
| 2011/0226272 A1 | 9/2011 | Focht et al. |

FOREIGN PATENT DOCUMENTS

| | | |
|---|---|---|
| DE | 196 50 952 A | 6/1998 |
| DE | 198 54 086 A | 5/2000 |
| EP | 0 078138 A2 | 5/1983 |
| EP | 0 331617 B | 4/1992 |
| EP | 1 108421 A2 | 6/2001 |
| EP | 1 005849 B1 | 9/2001 |
| EP | 1064918 B1 | 9/2002 |
| EP | 0 907345 B1 | 5/2003 |
| GB | 1277324 A | 6/1972 |
| JP | 2000229817 A | 8/2000 |
| JP | 2002-128639 A | 5/2002 |
| JP | 2002-138010 A | 5/2002 |
| WO | WO 90/13283 A1 | 11/1990 |
| WO | WO 94/10973 A1 | 5/1994 |
| WO | WO 97/17938 A1 | 5/1997 |
| WO | WO 98/27193 A1 | 6/1998 |
| WO | WO 98/33477 | 8/1998 |
| WO | WO 99/38489 A1 | 8/1999 |
| WO | WO 99/38491 A1 | 8/1999 |
| WO | WO 00/75240 A1 | 12/2000 |
| WO | WO 01/01931 A3 | 1/2001 |
| WO | WO 01/23517 A1 | 4/2001 |
| WO | WO 01/70193 A2 | 9/2001 |
| WO | WO 01/70926 A1 | 9/2001 |
| WO | WO 02/100358 A1 | 12/2002 |
| WO | WO 03/055456 A1 | 7/2003 |
| WO | WO 03/105796 A1 | 12/2003 |
| WO | WO 2004/018609 A1 | 3/2004 |
| WO | WO 2004/026276 A1 | 4/2004 |
| WO | WO 2004/050055 A1 | 6/2004 |
| WO | WO 2005/067875 A1 | 7/2005 |

OTHER PUBLICATIONS

C.J. van Oss, "Coacervation, Complex-Coacervation and Flocculation," J. Dispersion Science and Technology, vol. 9 (5, 6), 1988-89, P 561-573, nma.

D.J. Burgess, "Practical Analysis of Complex Coacervate Systems," J. of Colloid Anti Interface Science, vol. 140, No. 1, Nov. 1990, pp. 227-238.

KOBO Brochure, "Treated Pigments" (May 2000).

* cited by examiner

MILD MULTI-PHASED PERSONAL CARE COMPOSITION

CROSS REFERENCE TO RELATED APPLICATION(S)

This application claims the benefit of provisional application No. 60/548,739, filed Feb. 27, 2004.

FIELD OF THE INVENTION

The present invention relates to a mild multi-phased personal care composition comprising a surfactant component comprising a surfactant or a mixture of surfactants; wherein said mild multi-phased personal care composition has a Structured Domain Volume Ratio of at least about 45%.

BACKGROUND OF THE INVENTION

Personal care compositions are becoming more popular in the United States and around the world. Personal care compositions are well known and widely used. Desirable personal care composition must meet a number of criteria. For example, in order to be acceptable to consumers, a personal care composition must exhibit good cleaning properties, must exhibit good lathering characteristics, must be mild to the skin (not cause drying or irritation) and preferably should even provide a conditioning benefit to the skin. Personal care compositions have also been used to alter the color and appearance of skin.

Personal care compositions that attempt to provide skin-conditioning benefits are known. Many of these compositions are aqueous systems comprising an emulsified conditioning oil or other similar materials in combination with a lathering surfactant. Although these products provide both conditioning and cleansing benefits, it is often difficult to formulate a product that deposits sufficient amount of skin conditioning agents on skin during use. In order to combat emulsification of the skin conditioning agents by the cleansing surfactant, large amounts of the skin conditioning agent are added to the compositions. However, this introduces another problem associated with these dual cleansing and conditioning products. Raising the level of skin conditioning agent in order to achieve increased deposition negatively affects product lather performance and stability.

One attempt at providing conditioning and cleansing benefits from a personal cleansing product while maintaining stability has been the use of dual-chamber packaging. These packages comprise separate cleansing compositions and conditioning compositions, and allow for the co-dispensing of the two in a single or dual stream. The separate conditioning and cleansing compositions thus remain physically separate and stable during prolonged storage and just prior to application, but then mix during or after dispensing to provide conditioning and cleansing benefits from a physically stable system. Although such dual-chamber delivery systems provide improved conditioning benefits over the use of conventional systems, it is often difficult to achieve consistent and uniform performance because of the uneven dispensing ratio between the cleansing phase and the conditioning phase from these dual-chamber packages. Additionally, these packaging systems add considerable cost to the finished product.

Accordingly, the need still remains for stable, mild, multi-phased personal care composition that provides cleansing with increased lather longevity and improved lathering characteristics, and skin benefits such as silky skin feel, improved soft skin feel, and improved smooth skin feel. The need also remains for a personal care composition comprising two phases in physical contact that remain stable for long periods of time.

It is therefore an object of the present invention to provide a mild multi-phased personal care composition comprising visually distinct phase comprising a surfactant having a structured domain combined with a second visually distinct phase that can comprise high levels of benefit components that are not emulsified in the composition but comprised in a separate benefit phase so that the benefit components can be deposited at higher levels while at the same time maintaining superior lather performance.

SUMMARY OF THE INVENTION

The present invention relates to a multi-phased personal care composition comprising at least two visually distinct phases; wherein at least one phase comprises a cleansing phase comprising a surfactant component comprising a surfactant or a mixture of surfactants; wherein said mild personal care composition has a Structured Domain Volume Ratio of at least about 45%; wherein said phases form a pattern; and wherein said phases are packaged in physical contact with one another and maintain stability.

The present invention further relates to a mild multi-phase personal care composition comprising at least two visually distinct phases; wherein at least one phase comprises a cleansing phase comprising a surfactant component comprising a surfactant or a mixture of surfactants; wherein said surfactant component further comprises an opaque structured domain; wherein said opaque structured domain is lamellar phase; wherein said mild multi-phased personal care composition has a Structured Domain Volume Ratio of at least about 45%; wherein the visually distinct phases form a pattern; and wherein said visually distinct phases are packaged in physical contact with one another and maintain stability.

The present invention is also directed to a method of cleansing, moisturizing and delivering skin benefit agents and particles to the skin by applying to the skin a composition as described above.

DETAILED DESCRIPTION OF THE INVENTION

The mild multi-phased personal care composition of the present invention comprises at least two visually distinct phases; wherein the phases form a pattern; wherein said composition comprises a surfactant component comprising a surfactant or a mixture of surfactants; wherein said mild multi-phased personal care composition has a Structured Domain Volume Ratio of at least about 45%.

These and other essential limitations of the compositions and methods of the present invention, as well as many of the optional ingredients suitable for use herein, are described in detail hereinafter.

The term "anhydrous" as used herein, unless otherwise specified, refers to those compositions or materials containing less than about 10%, more preferably less than about 5%, even more preferably less than about 3%, even more preferably zero percent, by weight of water.

The term "ambient conditions" as used herein, refers to surrounding conditions at one (1) atmosphere of pressure, 50% relative humidity, and 25° C.

The term "cosmetically efficacious level" as used herein, is a level conferring a benefit during use of the composition.

The term "Consistency value" or "k" as used herein is a measure of viscosity and is used in combination with Shear Index, to define viscosity for materials whose viscosity is a function of shear. The measurements are made at 25° C. and the units are poise (equal to 100 centipoise).

The term "domain", as used herein means a volume of material, component, composition or phase comprising a molecular mixture which can be concentrated but not further separated by physical forces such as ultracentrifugation. For example, surfactant lamellar, surfactant micellar, surfactant crystal, oil, wax, water-glycerine mixture, hydrated hydrophilic polymer all constitute domains which can be concentrated and observed by ultracentrifugation, but which cannot be further separated into distinct molecular components by the same forces.

The term "hydrophobically modified interference pigment" or "HMIP", as used herein, means a portion of the interference pigment surface has been coated, including both physical and chemical bonding of molecules, with a hydrophobic material.

The term "interference pigment", as used herein, means a pigment with pearl gloss prepared by coating the surface of a particle substrate material (generally platelet in shape) with a thin film. The thin film is a transparent or semitransparent material having a high refractive index. The higher refractive index material shows a pearl gloss resulting from mutual interfering action between reflection and incident light from the platelet substrate/coating layer interface and reflection of incident light from the surface of the coating layer.

By the term "multi-phased" or "multi-phase" as used herein, is meant that the at least two phases herein occupy separate but distinct physical spaces inside the package in which they are stored, but are in direct contact with one another (i.e., they are not separated by a barrier and they are not emulsified or mixed to any significant degree). In one preferred embodiment of the present invention, the "multi-phased" personal care compositions comprising at least two phases are present within the container as a visually distinct pattern. The pattern results from the mixing or homogenization of the "multi-phased" composition. The patterns include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, and tessellated. Preferably the pattern is selected from the group consisting of striped, geometric, marbled and combinations thereof.

In a preferred embodiment the striped pattern may be relatively uniform and even across the dimension of the package. Alternatively, the striped pattern may be uneven, i.e. wavy, or may be non-uniform in dimension. The striped pattern does not need to necessarily extend across the entire dimension of the package. The phases may be various different colors, or include particles, glitter or pearlescence.

The term "mild multi-phased personal care composition" as used herein, refers to compositions intended for topical application to the skin or hair.

The term "opaque" structured domain as used herein refers to a surfactant domain with ordered structures (e.g., lamellar structure, vesicule structure, cubic structure, etc.) and it is visually opaque to a naked eye in a 10 mm inner diameter plastic centrifuge tube after the Ultracentrifugation Method described herein.

The term "phases" as used herein, refers to a region of a composition having one average composition, as distinct from another region having a different average composition, wherein the regions are visible to the naked eye. This would not preclude the distinct regions from comprising two similar phases where one phase could comprise pigments, dyes, particles, and various optional ingredients, hence a region of a different average composition.

The term "Shear Index" or "n" as used herein is a measure of viscosity and is used in combination with Consistency value, to define viscosity for materials whose viscosity is a function of shear. The measurements are made at 25° C. and the units are dimensionless.

The term "stable" as used herein, unless otherwise specified, refers to compositions that maintain at least two "separate" phases when sitting in physical contact at ambient conditions for a period of at least about 180 days wherein the distribution of the two phases in different locations in the package does not change over time.

By "separate" is meant that the well-distributed nature of the visually distinct phases is compromised, such that larger regions of at least one phase collect until the balanced dispensed ratio of the two or more compositions relative to each other is compromised.

The phrase "substantially free of" as used herein, means that the composition comprises less than about 3%, preferably less than about 1%, more preferably less than about 0.5%, even more preferably less than about 0.25%, and most preferably less than about 0.1%, by weight of the composition, of the stated ingredient.

The Vaughan Solubility Parameter (VSP) as used herein is a parameter used to define the solubility of hydrophobic compositions comprising hydrophobic materials. Vaughan Solubility parameters are well known in the various chemical and formulation arts and typically have a range of from about 5 to about 25 $(cal/cm^3)^{1/2}$.

All percentages, parts and ratios as used herein are by weight of the total composition, unless otherwise specified. All such weights as they pertain to listed ingredients are based on the active level and, therefore do not include solvents or by products that may be included in commercially available materials, unless otherwise specified.

The mild multi-phased personal care composition compositions and methods of the present invention can comprise, consist of, or consist essentially of, the essential elements and limitations of the invention described herein, as well as any additional or optional ingredients, components, or limitations described herein or otherwise useful in personal care compositions intended for topical application to the hair or skin.

Product Form

The mild multi-phased personal care composition of the present invention is typically in the form of a liquid. The term "liquid" as used herein means that the composition is generally flowable to some degree. "Liquids", therefore, can include liquid, semi-liquid, cream, lotion or gel compositions intended for topical application to skin. The compositions typically exhibit a viscosity of from about 1,500 cps to about 1,000,000 cps, as measured by the Viscosity Method as described in copending application Ser. No. 60/542,710, filed on Feb. 6, 2004. These compositions contain at least two phases, which are described in greater detail hereinafter.

When evaluating a mild multi-phased personal care composition, by the methods described herein, preferably each individual phase is evaluated prior to combining, unless otherwise indicated in the individual methodology. However, if the phases are combined, each phase can be separated by centrifugation, ultracentrifugation, pipetting, filtering, washing dilution, or combination thereof, and then the separate components or phases can be evaluated. Preferably, the separation means is chosen so that the resulting separated components being evaluated is not destroyed, but is representative of the component as it exists in the mild multi-phased personal care composition. All of the product forms contemplated for purposes of defining the compositions and methods of the present invention are rinse-off formulations, by which is meant the product is applied topically to the skin or hair and then subsequently (i.e., within minutes) the skin or hair is rinsed with water, or otherwise wiped off using a substrate or other suitable removal means with deposition of a portion of the composition.

Phases

The mild multi-phase personal care compositions of the present invention comprises at least two phases, wherein in the composition can have a first phase a second phase and so on. The ratio of a first phase to a second phase is about 90:10 to about 10:90, preferably about 80:20 to about 20:80, more preferably about 70:30 to about 30:70, even more preferably about 60:40 to about 40:60, still more preferably about 50:50. Each phase could be one or more of the following nonlimiting examples including: a cleansing phase, a benefit phase, and a non-lathering structured aqueous phase, which are described in greater detail hereinafter.

Cleansing Phase

The mild multi-phase personal care composition of the present invention can comprise a cleansing phase. The cleansing phase comprises a surfactant component comprising a surfactant or a mixture of surfactants.

Surfactant Component

The surfactant component comprises a surfactant or a mixture of surfactants. The surfactant component comprises surfactants suitable for application to the skin or hair. Suitable surfactants for use herein include any known or otherwise effective cleansing surfactant suitable for application to the skin, and which is otherwise compatible with the other essential ingredients in the mild multi-phased personal care composition including water. These surfactants include anionic, nonionic, cationic, zwitterionic or amphoteric surfactants, soap or combinations thereof.

Preferably the surfactant component comprises a mixture of at least one nonionic surfactant, at least one anionic surfactant and at least one amphoteric surfactant. The general categories of alkyl amines and alkanolamines are less preferred surfactants, because such surfactants tend to be less mild than other suitable surfactants. In a preferred embodiment of the present invention, the mild multi-phased personal care composition is substantially free of alkyl amines and alkanolamines.

The surfactant component in the present invention exhibits Non-Newtonian shear thinning behavior. Preferably, the mild multi-phased personal care composition has a viscosity of greater than about 1,500 centipoise ("cps"), more preferably greater than about 5,000 cps, even more preferably greater than about 10,000 cps, and still more preferably greater than about 20,000 cps, as measured by the Viscosity Method described in copending application Ser. No. 60/542,710 filed on Feb. 6, 2004.

The surfactant component comprises a structured domain comprising a structured surfactant system. The structured domain enables the incorporation of high levels of benefit components in a separate visually distinct phase that are not emulsified in the composition but suspended. In a preferred embodiment the structured domain is an opaque structured domain. The opaque structured domain is preferably a lamellar phase. The lamellar phase produces a lamellar gel network that is a type of colloidal system. The lamellar phase provides resistance to shear, adequate yield to suspend particles and droplets and at the same time provides long term stability, since they are thermodynamically stable. The lamellar phase yields a higher viscosity without the need for viscosity modifiers.

Preferably, the surfactant component has a Yield Point of greater than about 0.1 Pascal (Pa), more preferably greater than about 0.5 Pascal, even more preferably greater than about 1.0 Pascal, still more preferably greater than about 2.0 Pascal, still even more preferably greater than about 5 Pascal, and even still even more preferably greater than about 10 Pascal as measured by the Yield Point Method described hereafter.

The mild multi-phased personal care composition comprising the surfactant component has a Structured Domain Volume Ratio of at least about 45%, preferably at least about 50%, more preferably at least about 55%, even more preferably at least about 60%, still more preferably at least about 65%, still even more preferably at least about 70%, and still even still more preferably at least about 80% as measured by the Ultracentrifugation Method described hereafter.

The mild multi-phased personal care composition preferably comprises a surfactant component at concentrations ranging from about 5% to about 99%, preferably from about 10% to about 99%, more preferably from about 25% to about 90%, even more preferably from about 35% to about 88%, still more preferably from about 40% to about 85%, and still even more preferably from about 45% to about 85%, by weight of the mild multi-phased personal care composition. The preferred pH range of the mild multi-phased personal care composition is from about 5 to about 8, more preferably about 6.

The surfactant component has a Total Lather Volume of at least about 600 ml, preferably greater than about 800 ml, more preferably greater than about 1000 ml, even more preferably greater than about 1200 ml, still more preferably greater than about 1500 ml, and still even more preferably greater than about 2000 ml, as measured by the Lather Volume Test described hereafter. The surfactant component preferably has a Flash Lather Volume of at least about 300 ml, preferably greater than about 400 ml, even more preferably greater than about 500 ml, as measured by the Lather Volume Test described hereafter.

The structured domain has a Total Lather Volume of at least about 450 ml, preferably greater than about 500 ml, more preferably greater than about 600 ml, even more preferably greater than about 800 ml, still more preferably greater than about 1000 ml, and still even more preferably greater than about 1250 ml, as measured by the Lather Volume Test described hereafter. The structured domain preferably has a Flash Lather Volume of at least about 200 ml, preferably greater than about 250 ml, even more preferably greater than about 300 ml, as measured by the Lather Volume Test described hereafter.

Non-ionic Surfactants

The mild multi-phased personal care composition preferably comprises at least one nonionic surfactant. Preferably the nonionic surfactant has an HLB from about 1.0 to about 15.0, preferably from about 3.4 to about 15.0, more preferably from about 3.4 to about 9.5, even more preferably from about 3.4 to about 5.0. The mild multi-phased personal care composition preferably comprises a nonionic surfactant at concentrations ranging from about 0.01% to about 50%, more preferably from about 0.10% to about 10%, and even more preferably from about 0.5% to about 5.0%, by weight of the surfactant component.

Non-limiting examples of nonionic surfactants for use in the compositions of the present invention are disclosed in McCutcheon's, Detergents and Emulsifiers, North American edition (1986), published by allured Publishing Corporation; and McCutcheon's, Functional Materials, North American Edition (1992).

Nonionic surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Non-limiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, and mixtures thereof. In a preferred embodiment the nonionic surfactant is selected from the group consisting of glyceryl monohydroxystearate, Steareth-2, hydroxy stearic acid, propylene glycol stearate, PEG-2 stearate, sorbitan monostearate, glyceryl stearate; laureth-2 and mixtures thereof. In a preferred embodiment the nonionic surfactant is Steareth-2.

Nonionic lathering surfactants also useful herein include, lauramine oxide, cocoamine oxide.

The balance between the hydrophilic and lipophilic moieties in a surfactant molecule is used as a method of classification (hydrophile-lipophile balance, HLB). The HLB values for commonly-used surfactants are readily available in the literature (eg. Handbook of Pharmaceutical Excipients, The Pharmaceutical Press. London, 1994). The HLB system was originally devised by Griffin (J. Soc. Cosmetic Chem., 1, 311, 1949). Griffin defined the HLB value of a surfactant as the mol % of the hydrophilic groups divided by 5, where a completely hydrophilic molecule (with no non-polar groups) had an HLB value of 20.

Anionic Surfactants

The mild multi-phased personal care composition preferably comprises at least one anionic surfactant. The mild multi-phased personal care composition preferably comprises an anionic surfactant at concentrations ranging from about 1% to about 50%, more preferably from about 4% to about 30%, even more preferably from about 5% to about 25%, by weight of the surfactant component.

Preferably the anioninc surfactant is selected from the group consisting of alkyl ether sulfates, alkyl sulfonates and mixtures thereof.

Anionic surfactants suitable for use in the mild multi-phased personal care composition composition include alkyl and alkyl ether sulfates. These materials have the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates are typically made as condensation products of ethylene oxide and monohydric alcohols having from about 8 to about 24 carbon atoms. Preferably, R has from about 10 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, preferably from about 3 to about 5, and more preferably with about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the mild multi-phased personal care composition composition are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants include water-soluble salts of the organic, sulfuric acid reaction products of the general formula $[R^1-SO_3-M]$, wherein $R^1$ is chosen from the group consisting of a straight or branched chain, saturated aliphatic hydrocarbon radical having from about 8 to about 24, preferably about 10 to about 18, carbon atoms; and M is a cation. Suitable examples are the salts of an organic sulfuric acid reaction product of a hydrocarbon of the methane series, including iso-, neo-, ineso-, and n-paraffins, having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Other suitable surfactants are described in *McCutcheon's. Emulsifiers and Detergents, 1989 Annual*, published by M. C. Publishing Co., and in U.S. Pat. No. 3,929,678.

Preferred anionic surfactants for use in the mild multi-phased personal care composition composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Anionic surfactants with branched alkyl chains such as sodium trideceth sulfate, for example, are preferred in some embodiments. Mixtures of anionic surfactants may be used in some embodiments.

Amphoteric Surfactants

The mild multi-phased personal care composition preferably comprises at least one amphoteric surfactant. The mild multi-phased personal care composition preferably comprises an amphoteric surfactant at concentrations ranging from about 1% to about 50%, more preferably from about 2% to about 30%, even more preferably from about 3% to about 25%, by weight of the surfactant component.

Amphoteric surfactant suitable for use in the present invention include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378.

Amphoacetates and diamphoacetates may also be used.

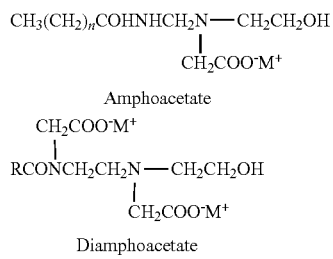

Amphoacetate

Diamphoacetate

Amphoacetates and diamphoacetates conform to the formulas (above) where R is an aliphatic group of 8 to 18 carbon atoms. M is a cation such as sodium, potassium, ammonium, or substituted ammonium. Sodium lauroamphoacetate, sodium cocoamphoactetate, disodium lauroamphoacetate, and disodium cocodiamphoacetate are preferred in some embodiments.

Additional surfactant from the classes of zwitterionic surfactant, and/or cationic surfactant, may be incorporated in the mild multi-phased personal care composition.

Zwitterionic surfactants suitable for use in the mild multi-phased personal care composition include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

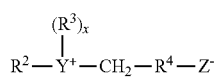

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use in the mild multi-phased personal care composition include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH$(CH_2)_3$ radical is attached to the nitrogen atom of the betaine are also useful in this invention.

Cationic surfactants can also be used in the mild multi-phased personal care composition, but are generally less preferred, and preferably represent less than about 5% by weight of the mild multi-phased personal care composition.

Electrolyte

The electrolyte, if used, can be added per se to the mild multi-phased personal care composition or it can be formed in situ via the counterions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium or ammonium chloride or sodium or ammonium sulfate. A preferred electrolyte is sodium chloride. The electrolyte is preferably added to the surfactant component of the composition.

The electrolyte, when present, should be present in an amount, which facilitates formation of the stable composition (Non-Newtonian shear thinning behavior). Generally, this amount is from about 0.1% by weight to about 15% by weight, preferably from about 1% to about 6% by weight of the mild multi-phased personal care, but may be varied if required.

Benefit Phase

The mild multi-phase personal care compositions of the present invention can comprise a benefit phase. The benefit phase in the present invention is preferably anhydrous. The benefit phase comprises hydrophobic compositions comprising hydrophobic components. The benefit phase comprises from about 20% to about 100%, preferably at least about 35%, most preferably at least about 50% of a hydrophobic component. The hydrophobic compositions suitable for use in the present invention have a Vaughan Solubility Parameter, as described in copending application Ser. No. 60/542,710, filed on Feb. 6, 2004, of from about 5 to about 15. The hydrophobic compositions are preferably selected among those having defined rheological properties as described in copending application Ser. No. 60/542,710, filed on Feb. 6, 200, including selected Consistency value (k) and Shear Index (n). These preferred rheological properties are especially useful in providing the mild multi-phased personal care composition compositions with improved deposition of hydrophobic components on the skin.

Nonlimiting examples of hydrophobic components suitable for use herein can include a variety of hydrocarbons, oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, polyglycerin fatty acid esters, lanolin and its derivatives, wax esters, beeswax derivatives, sterols and phospholipids, vitamins and pro-vitamins and combinations thereof.

Non-limiting examples of hydrocarbon oils and waxes suitable for use herein include petrolatum, mineral oil, microcrystalline waxes, polyalkenes, paraffins, cerasin, ozokerite, polyethylene, perhydrosqualene, and combinations thereof.

Non-limiting examples of silicone oils suitable for use as hydrophobic components herein include dimethicone copolyol, dimethylpolysiloxane, diethylpolysiloxane, mixed $C_1$-$C_{30}$ alkyl polysiloxanes, phenyl dimethicone, dimethiconol, and combinations thereof. Preferred are non-volatile silicones selected from dimethicone, dimethiconol, mixed $C_1$-$C_{30}$ alkyl polysiloxane, and combinations thereof. Nonlimiting examples of silicone oils useful herein are described in U.S. Pat. No. 5,011,681 (Ciotti et al.).

Non-limiting examples of diglycerides and triglycerides suitable for use as hydrophobic components herein include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof.

Non-limiting examples of acetoglyceride esters suitable for use as hydrophobic components herein include acetylated monoglycerides.

Non-limiting examples of alkyl esters suitable for use as hydrophobic components herein include isopropyl esters of fatty acids and long chain esters of long chain (i.e. $C_{10}$-$C_{24}$) fatty acids, e.g. cetyl ricinoleate, non-limiting examples of which incloude isopropyl palmitate, isopropyl myristate, cetyl riconoleate and stearyl riconoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use as hydrophobic components herein include oleyl myristate, oleyl stearate, oleyl oleate, and combinations thereof.

Non-limiting examples of polyglycerin fatty acid esters suitable for use as hydrophobic components herein include decaglyceryl distearate, decaglyceryl diisostearate, decaglyceryl monomyriate, decaglyceryl monolaurate, hexaglyceryl monooleate, and combinations thereof.

Non-limiting examples of lanolin and lanolin derivatives suitable for use as hydrophobic components herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Still other suitable hydrophobic components include milk triglycerides (e.g., hydroxylated milk glyceride) and polyol fatty acid polyesters.

Still other suitable hydrophobic components include wax esters, non-limiting examples of which include beeswax and beeswax derivatives, spermaceti, myristyl myristate, stearyl stearate, and combinations thereof. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof.

In a preferred embodiment the mild multi-phased personal care composition can comprise a multi-phase composition having a benefit phase; wherein the benefit phase preferably can comprise one or more hydrophobic components, wherein at least 20% by weight of the hydrophobic components are selected from petrolatum, mineral oil, sunflower seed oil, micro-crystalline waxes, paraffins, ozokerite, polyethylene, polybutene, polydecene and perhydrosqualene dimethicones, cyclomethicones, alkyl siloxanes, polymethylsiloxanes and methylphenylpolysiloxanes, lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, castor oil, soy bean oil, maleated soy bean oil, safflower oil, cotton seed oil, corn oil, walnut oil, peanut oil, olive oil, cod liver oil, almond oil, avocado oil, palm oil and sesame oil, and combinations thereof. More preferably, at least about 50% by weight of the hydrophobic components are selected from the groups of petrolatum, mineral oil, paraffins, polyethylene, polybutene, polydecene, dimethicones, alkyl siloxanes, cyclomethicones, lanolin, lanolin oil, lanolin wax. The remainder of the hydrophobic components are preferably selected from: isopropyl palmitate, cetyl riconoleate, octyl isononanoate, octyl palmitate, isocetyl stearate, hydroxylated milk glyceride and combinations thereof.

Non-Lathering Structured Aqueous Phase

The mild multi-phase personal care compositions of the present invention can comprise a non-lathering structured aqueous phase. The non-lathering structured aqueous phase of the composition comprises a water structurant and water. The non-lathering structured aqueous phase can be hydrophilic and in a preferred embodiment the non-lathering structured aqueous phase is a hydrophilic gelled water phase. In addition, the non-lathering structured aqueous phase typically comprises less than about 5%, preferably less than about 3%, and more preferably less than about 1%, by weight of the non-lathering structured aqueous phase, of a surfactant. In one embodiment of the present invention, the non-lathering structured aqueous phase is free of surfactant.

The non-lathering structured aqueous phase preferably produces a Total Lather Volume of greater than about 350 ml, more preferably greater than about 330 ml, even more preferably greater than about 300 ml, as measured by the Lather Volume Test described in copending application Ser. No. 60/532,798, filed on Dec. 24, 2003. The non-lathering structured aqueous phase preferably produces a Flash Lather Volume of greater than about 150 ml, preferably greater than about 130 ml, even more preferably greater than about 100 ml, as measured by the Lather Volume Test described in copending application Ser. No. 60/532,798, filed on Dec. 24, 2003.

Preferably, the non-lathering structured aqueous phase exhibits a Yield Point of at least about 0.1 Pa, preferably at least about 1 Pa, more preferably at least about 10 Pa, as measured by the Yield Point Method described in copending application Ser. No. 60/542,710, filed on Feb. 6, 2004. Preferably, the non-lathering structured aqueous phase exhibits a Water Mobility of less than about 2.5 seconds, more preferably less than about 2 seconds, and even more preferably less than about 1 second, as measured by the Water Mobility Method described in copending applications Ser. No. 60/532,798, filed on Dec. 24, 2003.

Preferably, the non-lathering structured aqueous phase exhibits a Correlated Haze of less than about 50% Correlated Haze, more preferably less than about 30% Correlated Haze, even more preferably less than about 20% Correlated Haze, and still more preferably less than about 10% Correlated Haze as measured by the Correlated Haze Index Method described in copending application Ser. No. 60/542,710 filed on Feb. 6, 2004.

The non-lathering structured aqueous phase has a preferred rheology profile as defined by Consistency Value (k) and Shear Index (n). Preferred Consistency Values of the non-lathering structured aqueous phase are from about 10 to about 100,000 poise/(1/s), preferably from about 10 to about 10,000 poise/(1/s), and more preferably from about 100 to about 1,000 poise/(1/s). The Shear Index of the non-lathering structured aqueous phase typically ranges from about 0.1 to about 0.8, preferably from about 0.1 to about 0.5, and more preferably from about 0.20 to about 0.4.

The Shear Index (n) and Consistency Value (k) are well-known and accepted industry standards for reporting the viscosity profile of compositions having a viscosity that is a function of an applied shear rate. The methodology used to obtain these values was described in greater detail in copending application Ser. No. 60/542,710 filed on Feb. 6, 2004.

The non-lathering structured aqueous phase of the present invention comprises from about 30% to about 99%, by weight of the non-lathering structured aqueous phase, of water. The non-lathering structured aqueous phase generally comprises more than about 50%, preferably more than about 60%, even more preferably more than about 70%, still more preferably more than about 80%, by weight of the non-lathering structured aqueous phase, of water.

The non-lathering structured aqueous phase will typically have a pH of from about to about 8, more preferably about 7. The non-lathering structured aqueous phase can optionally comprise a pH regulator to facilitate the proper pH range.

The non-lathering structured aqueous phase can have a net cationic charge, net anionic charge, or neutral charge. In a preferred embodiment, the non-lathering structured aqueous phase has a net anionic charge.

The non-lathering structured aqueous phase of the present compositions can further comprise optional ingredients such as those described hereinafter. Preferred optional ingredients for the non-lathering structured aqueous phase include pigments, pH regulators, and preservatives. In one embodiment, the non-lathering structured aqueous phase comprises a water structurant (e.g. acrylates/vinyl isodecanoate crosspolymer), water, a pH regulator (e.g. triethanolamine), and a preservative (e.g. 1,3-dimethylol-5,5-dimethylhydantoin ("DM-DMH" available from Lonza under the trade name GLY-DANT®)).

A) Water Structurant

The non-lathering structured aqueous phase comprises from about 0.1% to about 30%, preferably from about 0.5% to about 20%, more preferably from about 0.5% to about 10%, and even more preferably from about 0.5% to about 5%, by weight of the non-lathering structured aqueous phase, of a water structurant.

The water structurant is typically selected from the group consisting of inorganic water structurants, charged polymeric water structurants, water soluble polymeric structurants, associative water structurants, and mixtures thereof.

Non-limiting examples of inorganic water structurants for use in the mild multi-phased personal care composition composition include silicas, clays such as a synthetic silicates (Laponite XLG and Laponite XLS from Southern Clay), or mixtures thereof.

Non-limiting examples of charged polymeric water structurants for use in the mild multi-phased personal care composition include Acrylates/Vinyl Isodecanoate Crosspolymer (Stabylen 30 from 3V), Acrylates/C10-30 Alkyl Acrylate Crosspolymer (Pemulen TR1 and TR2), Carbomers, Ammonium Acryloyldimethyltaurate/VP Copolymer (Aristoflex AVC from Clariant), Ammonium Acryloyldimethyltaurate/Beheneth-25 Methacrylate Crosspolymer (Aristoflex HMB from Clariant), Acrylates/Ceteth-20 Itaconate Copolymer (Structure 3001 from National Starch), Polyacrylamide (Sepigel 305 from SEPPIC), or mixtures thereof.

Non-limiting examples of water soluble polymeric structurants for use in the mild multi-phased personal care composition composition include cellulosic gel, hydroxypropyl starch phosphate (Structured XL from National Starch), polyvinyl alcohol, or mixtures thereof.

Nonlimiting examples of associative water structurants for use in the the mild multi-phased personal care composition include xanthum gum, gellum gum, pectin, alginate, or mixtures thereof.

Particle

The mild multi-phased personal care composition can comprise a particle. Water insoluble solid particle of various shapes and densities is useful. In a preferred embodiment, the particle tends to have a spherical, an oval, an irregular, or any other shape in which the ratio of the largest dimension to the smallest dimension (defined as the Aspect Ratio) is less than about 10. More preferably, the Aspect Ratio of the particle is less than about 8, still more preferably the Aspect Ratio of the particle is less than about 5.

The particle of the present invention has a particle size (volume average based on the particle size measurement described in copending application Ser. No. 60/542,710, filed on Feb. 6, 2004) of less than about 100 µm, preferably less than about 80 µm, and more preferably the particle size of less than about 60 µm.

The particle of the present invention preferably has a particle size of greater than about 0.1 µm, preferably a particle size of greater than about 0.5 µm, more preferably, a particle size greater than about 1 µm, still more preferably a particle size greater than about 2 µm, even more preferably a particle size greater than about 3 µm, and still even more preferably a particle size greater than about 4 µm.

The particle has a diameter from about 1 µm to about 70 µm, more preferably from about 2 µm to about 65 µm, and even more preferably from about 2 µm to about 60 µm in diameter.

The mild multi-phased personal care composition of the present invention comprises the particle at a cosmetically efficacious level. Preferably, the particles are present from at least about 0.1% by weight of the composition, more preferably at least about 0.2% by weight of composition, even more preferably at least about 0.5%, still more preferably at least about 1%, and even still more preferably at least 2% by weight of composition. In the mild multi-phased personal care composition of the present invention, preferably the particles comprises no more than about 50% by weight of composition, more preferably no more than about 30%, still more preferably no more than about 20%, and even more preferably no more than about 10% by weight of composition.

Preferably, the particle will also have physical properties which are not significantly affected by typical processing of the composition. Preferably, a particle having a melting point greater than about 70° C. is used, more preferably having a melting point greater than about 80° C., and even more preferably having a melting point of greater than about 95° C. is used. As used herein, melting point would refer to the temperature at which the particle transitions to a liquid or fluid state or undergoes significant deformation or physical property changes. In addition, many of the particles of present invention are cross-linked or have a cross-linked surface membrane. These particles do not exhibit a distinct melting point. Cross-linked particles are also useful as long as they are stable under the processing and storage conditions used in the making of compositions.

The particles that can be present in the present invention can be natural, synthetic, or semi-synthetic. In addition, hybrid particles can also be present. Synthetic particles can made of either cross-linked or non cross-linked polymers. The particles of the present invention can have surface charges or their surface can be modified with organic or inorganic materials such as surfactants, polymers, and inorganic materials. Particle complexes can be present.

Non limiting examples of natural particles include various precipitated silica particles in hydrophilic and hydrophobic forms available from Degussa-Huls under the trade name Sipemet. Precipitated™, hydrophobic, synthetic amorphous silica, available from Degussa under the trade name Sipernet D11™ is a preferred particle. Snowtex colloidal silica particles available from Nissan Chemical America Corporation.

Nonlimiting examples of synthetic particles include nylon, silicone resins, poly(meth)acrylates, polyethylene, polyester, polypropylene, polystyrene, polyurethane, polyamide, epoxy resins, urea resins, and acrylic powders. Non limiting examples of useful particles are Microease 110S, 114S, 116 (micronized synthetic waxes), Micropoly 210, 250S (micronized polyethylene), Microslip (micronized polytetrafluoroethylene), and Microsilk (combination of polyethylene and polytetrafluoroethylene), all of which are available from Micro Powder, Inc. Additional examples include Luna (smooth silica particles) particles available from Phenomenex, MP-2200 (polymethylmethacrylate), EA-209 (ethylene/acrylate copolymer), SP-501(nylon-12), ES-830 (polymethly methacrylate), BPD-800, BPD-500 (polyurethane) particles available from Kobo Products, Inc. and silicone resins sold under the name Tospearl particles by GE Silicones. Ganzpearl GS-0605 crosslinked polystyrene (available from Presperse) is also useful.

Non limiting examples of hybrid particles include Ganzpearl GSC-30SR (Sericite & crosslinked polystyrene hybrid powder), and SM-1000, SM-200 (mica and silica hybrid powder available from Presperse).

Exfoliant Particle

The exfoliant particle is selected from the group consisting of polyethylene, microcryatalline wax, jojoba esters, amourphors silica, talc, tracalcium orthophosphate, or blends thereof, and the like. The exfoliant particle has a particle size dimension along the major axis of the particle of from about 100 microns to about 600 microns, preferably from about 100 microns to about 300 microns. The exfoliant particle has a hardness of less than about 4 Mohs, preferably less than about 3 Mohs. The hardness as so measured is a criterion of the resistance of a particular material to crushing. It is known as being a fairly good indication of the abrasive character of a particulate ingredient. Examples of materials arranged in increasing order of hardness according to the Moh scale are as follows: h(hardness)-1:talc; h-2: gypsum, rock salt, crystalline salt in general, barytes, chalk, brimstone; h-4: fluorite, soft phosphate, magnesite, limestone; h-5: apatite, hard phosphate, hard limestone, chromite, bauxite; h-6: feldspar, ilmenite, hornblendes; h-7: quartz, granite; h-8: topaz; h-9: corrundum, emery; and h-10: diamond.

Preferably, the exfoliant particle has a color distinct from the cleansing base. The exfoliant particle is preferably present at a level of less than about 10%, preferably less than about 5%, by wt of the composition.

Shiny Particles

The mild multi-phased personal care composition can comprise a shiny particle. In a preferred embodiment, the mild body wash composition comprises a multi-phase personal care composition that can comprise a shiny particle in at least one phase of the multi-phase personal care composition. Nonlimiting examples of shiny particles include the following: interference pigment, multi-layered pigment, metallic particle, solid and liquid crystals, or combinations thereof.

An interference pigment is a pigment with pearl gloss prepared by coating the surface of a particle substrate material with a thin film. The particle substrate material is generally platelet in shape. The thin film is a transparent or semitransparent material having a high refractive index. The high refractive index material shows a pearl gloss resulting from mutual interfering action between reflection and incident light from the platelet substrate/coating layer interface and reflection of incident light from the surface of the coating layer. The interference pigments of the multi-phased personal care compositions preferably comprises no more than about 20 weight percent of the composition, more preferably no more than about 10 weight percent, even more preferably no more than about 7 weight percent, and still more preferably no more than about 5 weight percent of the multi-phased personal care composition. The interference pigment of the multi-phased personal care composition preferably comprises at least about 0.1 weight percent of the multi-phased personal care composition, more preferably at least about 0.2 weight percent, even more preferably at least about 0.5 weight percent, and still more preferably at least about 1 weight percent by weight of the mild multi-phased personal composition. When pigment is applied and rinsed as described in the Pigment Deposition Tape Strip Method as described in copending application Ser. No. 60/469,075 filed on May 8, 2003, the deposited pigment on the skin is preferably at least 0.5 $\mu g/cm^2$, more preferably at least 1 $\mu g/cm^2$, and even more preferably at least 5 $\mu g/cm^2$.

The interference pigments of the present invention are platelet particulates. The platelet particulates preferably have a thickness of no more than about 5 µm, more preferably no more than about 2 µm, still more preferably no more than about 1 µm. The platelet particulates of the preferably have a thickness of at least about 0.02 µm, more preferably at least about 0.05 µm, even more preferably at least about 0.1 µm, and still more preferably at least about 0.2 µm.

The particle size determines the opacity and luster. The particle size is determined by measuring the diameter thickness of the particulate material. The term "diameter" as used herein, means the largest distance across the major axis of the particulate material. Diameter can be determined by any suitable method known in the art, such as particle size analyzer Mastersizer 2000 manufactured by Malvern Instruments. The interference pigment preferably have an average diameter not greater than about 200 µm, more preferably not greater than 100 µm, even more preferably not greater than about 80 µm, still more preferably not greater than than about 60 µm. The interference pigment preferably have a diameter of at least about 0.1 µm, more preferably at least about 1.0 µm, even more preferably at least about 2.0 µm, and still more preferably at least about 5.0 µm.

The interference pigment can comprise a multilayer structure. The centre of the particulates is a flat substrate with a refractive index (RI) normally below 1.8. A wide variety of particle substrates are useful herein. Nonlimiting examples are natural mica, synthetic mica, graphite, talc, kaolin, alumina flake, bismuth oxychloride, silica flake, glass flake, ceramics, titanium dioxide, $CaSO_4$, $CaCO_3$, $BaSO_4$, borosilicate and mixtures thereof, preferably mica, silica and alumina flakes.

A layer of thin film or a multiple layer of thin films are coated on the surface of a substrate described above. The thin films are made of highly refractive materials. The refractive index of these materials is normally above 1.8.

A wide variety of thin films are useful herein. Nonlimiting examples are $TiO_2$, $Fe_2O_3$, $SnO_2$, $Cr_2O_3$, ZnO, ZnS, ZnO, SnO, $ZrO_2$, $CaF_2$, $Al_2O_3$, BiOCl, and mixtures thereof or in the form of separate layers, preferably $TiO_2$, $Fe_2O_3$, $Cr_2O_3SnO_2$. For the multiple layer structures, the thin films can be consisted of all high refractive index materials or alternation of thin films with high and low RI materials with the high RI film as the top layer.

The interference color is a function of the thickness of thin film, the thickness for a specific color may be different for different materials. For $TiO_2$, a layer of 40 nm to 60 nm or a whole number multiple thereof gives silver color, 60 nm to 80 nm yellow color, 80 nm to 100 nm red color, 100 nm to 130 nm blue color, 130 nm to 160 nm green color. In addition to the interference color, other transparent absorption pigments can be precipitated on top of or simultaneously with the $TiO_2$ layer. Common materials are red or black iron oxide, ferric ferrocyanide, chromium oxide or carmine. It was found that the color of the interference pigment in addition to its brightness had a significant influence on human perception of skin tone. In general, preferred colors are silver, gold, red, green and mixtures thereof.

Nonlimiting examples of the interference pigments useful herein include those supplied by Persperse, Inc. under the trade name PRESTIGE®, FLONAC®; supplied by EMD Chemicals, Inc. under the trade name TIMIRON®, COLORONA®, DICHRONA® and XIRONA®; and supplied by Engelhard Co. under the trade name FLAMENCO®, TIMICA®, DUOCHROME®.

In an embodiment of the present invention the interference pigment surface is either hydrophobic or has been hydrophobically modified. The Particle Contact Angle Test as described in copending application Ser. No. 60/469,075 filed on May 8, 2003 is used to determine contact angle of interference pigments. The greater the contact angle, the greater the hydrophobicity of the interference pigment. The interference pigment of the present invention possess a contact angle of at least 60°, more preferably greater than 80°, even more preferably greater than 100°, still more preferably greater than 100°. The hydrophobically modified interference pigment or HMIP allows for the entrapment of the HMIP within the phases and greater deposition of the HMIP. Preferably the ratio of HMIP to a phase is 1:1 to about 1:70, more preferably 1:2 to about 1:50, still more preferably 1:3 to about 1:40 and most preferably 1:7 to about 1:35.

In an embodiment of the present invention the HMIP's are preferably entrapped within the hydrophobic composition. This necessitates that the hydrophobic composition particle size is generally larger than the HMIP. In a preferred embodiment of the invention, the hydrophobic composition particles contain only a small number of HMIPs per hydrophobic composition particles. Preferably this is less than 20, more preferably less than 10, most preferably less than 5. These parameters, the relative size of the benefit droplets to the HMIP and the approximate number of HMIP particles per hydrophobic composition particles, can be determined by using visual inspection with light microscopy.

The HMIP and the hydrophobic composition can be mixed into the composition via a premix or separately. For the case of separate addition, the hydrophobic pigments partition into the hydrophobic composition during the processing of the formulation. The HMIP of the present invention preferably has a hydrophobic coating comprising no more than about 20 weight percent of the total particle weight, more preferably no more than about 15 weight percent, even more preferably no more than about 10 weight percent. The HMIP of the present invention preferably has a hydrophobic coating comprising at least about 0.1 weight percent of the total particle weight, more preferably at least about 0.5 weight percent, even more preferably at least about 1 weight percent. Nonlimiting examples of the hydrophobic surface treatment useful herein include silicones, acrylate silicone copolymers, acrylate polymers, alkyl silane, isopropyl titanium triisostearate, sodium stearate, magnesium myristate, perfluoroalcohol phosphate, perfluoropolymethyl isopropyl ether, lecithin, carnauba wax, polyethylene, chitosan, lauroyl lysine, plant lipid extracts and mixtures thereof, preferably, silicones, silanes and stearates. Surface treatment houses include US Cosmetics, KOBO Products Inc., and Cardre Inc.

Optional Ingredients

A variety of suitable optional ingredients can be employed in the mild multi-phase personal care composition. Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. These optional materials can be used in any aspect of the compositions of the present invention, including each phase as described herein.

Non-limiting optional ingredients include humectants and solutes. A variety of humectants and solutes can be employed and can be present at a level of from about 0.1% to about 50%, preferably from about 0.5% to about 35%, and more preferably from about 2% to about 20%, by weight of the personal care composition. A preferred humectant is glycerin.

A preferred water soluble, organic material is selected from the group consisting of a polyol of the structure:

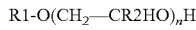

$$R1\text{-}O(CH_2\text{---}CR2HO)_nH$$

where R1=H, C1-C4 alkyl; R2=H, $CH_3$ and n=1-200; C2-C10 alkane diols; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerol, hexanetriol, propylene glycol, hexylene glycol and the like; polyethylene glycol; sugars and starches; sugar and starch derivatives (e.g. alkoxylated glucose); panthenol (including D-, L-, and the D,L-forms); pyrrolidone carboxylic acid; hyaluronic acid; lactamide monoethanolamine; acetamide monoethanolamine; urea, and ethanol amines of the general structure $(HOCH_2CH_2)_xNH_y$, where x=1-3; y=0-2, and x+y=3, and mixtures thereof. The most preferred polyols are selected from the group consisting of glycerine, polyoxypropylene(1) glycerol and polyoxypropylene(3) glycerol, sorbitol, butylene glycol, propylene glycol, sucrose, urea and triethanol amine.

Nonionic polyethylene/polypropylene glycol polymers are preferably used as skin conditioning agents. Polymers useful herein that are especially preferred are PEG-2M wherein x equals 2 and n has an average value of about 2,000 (PEG 2-M is also known as Polyox WSR® N-10 from Union Carbide and as PEG-2,000); PEG-5M wherein x equals 2 and n has an average value of about 5,000 (PEG 5-M is also known as Polyox WSR® 35 and Polyox WSR® N-80, both from Union Carbide and as PEG-5,000 and Polyethylene Glycol 200,000); PEG-7M wherein x equals 2 and n has an average value of about 7,000 (PEG 7-M is also known as Polyox WSR® (N-750 from Union Carbide); PEG-9M wherein x equals 2 and n has an average value of about 9,000 (PEG 9-M is also known as Polyox WSR® N-3333 from Union Carbide); PEG-14 M wherein x equals 2 and n has an average value of about 14,000 (PEG 14-M is also known as Polyox WSR-205 and Polyox WSR® N-3000 both from Union Carbide); and PEG-90M wherein x equals 2 and n has an average value of about 90,000. (PEG-90M is also known as Polyox WSR®-301 from Union Carbide.)

Other non limiting examples of these optional ingredients include vitamins and derivatives thereof (e.g., ascorbic acid, vitamin E, tocopheryl acetate, and the like); sunscreens; thickening agents (e.g., polyol alkoxy ester, available as Crothix from Croda); preservatives for maintaining the anti microbial integrity of the cleansing compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol).

Yield Point Method

A TA Instruments AR2000 Controlled Stress Rheometer can be used to determine the Yield Point of the surfactant component. For purpose herein, the Yield Point of the surfactant component or the mild multi-phased personal care composition is the amount of stress required to produce the onset of flow, where a significant increase in strain rate occurs. The determination is performed at 25° C. with a 4 cm diameter parallel plate measuring system and a 1 mm gap. The determination is performed via the programmed application of a shear stress continuous ramp (typically from about 0.1 Pa to about 500 Pa) over a time interval of 5 minutes, collecting 30 data points per decade of stress in an evenly spaced logarithmic stress progression. Stress results in a deformation of the sample, and a shear stress vs. strain curve can be created. The shear stress (Pa) is graphed on the x-axis vs. the strain on the y-axis using logarithmic scales for both axes. Mild multi-phased personal care compositions and surfactant components which are structured exhibit an initial region at low stresses that appears as a straight line when plotted in this way. The Yield Point is the stress point at which the observed strain deviates by greater than 10% from a regression line (i.e. from the predicted strain) extended from the initial straight line region on the log-log plot, determined by linear regression of log-log transformed stress-strain data points between 0.2-2.0 Pa, and continues to deviate by a substantially increasing and accelerating amount with each subsequent point, such that flow occurs. The surfactant component is measured either prior to combining in the composition, or after combining in the composition by separating the compositions by suitable non-destructive physical separation means.

Lather Volume Test

Lather volume of a cleansing phase, a surfactant component or a structured domain of a mild multi-phased personal care composition, is measured using a graduated cylinder and a rotating apparatus. A 1,000 ml graduated cylinder is used which is marked in 10 ml increments and has a height of 14.5 inches at the 1,000 ml mark from the inside of its base (for example, Pyrex No. 2982). Distilled water (100 grams at 25° C.) is added to the graduated cylinder. The cylinder is clamped in a rotating device, which clamps the cylinder with an axis of rotation that transects the center of the graduated cylinder. Inject 0.5 cc of a surfactant component or cleansing phase into the graduated cylinder onto the side of the cylinder, above the water line, and cap the cylinder. When the structured domain is evaluated, use only 0.25 cc, keeping everything else the same. The cylinder is rotated for 20 complete revolutions at a rate of about 10 revolutions per 18 seconds, and stopped in a vertical position to complete the first rotation sequence. A timer is set to allow 15 seconds for the lather thus generated to drain. After 15 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum foam height is 1,000 ml (even if the total foam height exceeds the 1,000 ml mark on the graduated cylinder). 30 seconds after the first rotation is completed, a second rotation sequence is commenced which is identical in speed and duration to the first rotation sequence. The second lather volume is recorded in the same manner as the first, after the same 15 seconds of drainage time. A third sequence is completed and the third lather volume is measured in the same manner, with the same pause between each for drainage and taking the measurement.

The lather result after each sequence is added together and the Total Lather Volume determined as the sum of the three measurements, in ml. The Flash Lather Volume is the result after the first rotation sequence only, in ml, i.e., the first lather volume. Compositions according to the present invention perform significantly better in this test than similar compositions in conventional emulsion form.

Ultracentrifugation Method:

The Ultracentrifugation Method is used to determine the percent of a structured domain or an opaque structured domain that is present in a mild multi-phased personal care composition that comprises a surfactant component. The method involves the separation of the composition through ultracentrifugation into separate but distinguishable layers. The mild multi-phased personal care composition of the present invention can have multiple distinguishable layers, for example a non-structured surfactant layer, a structured surfactant layer, and a benefit layer.

First, dispense about 4 grams of mild multi-phased personal care composition into Beckman Centrifuge Tube (11× 60 mm). Next, place the centrifuge tubes in an Ultracentrifuge (Beckman Model L8-M or equivalent) and set ultracentrifuge to the following conditions: 50,000 rpm, 18 hours, and 25° C.

After ultracentrifuging for 18 hours, determine the relative phase volume by measuring the height of each layer using an Electronic Digital Caliper (within 0.01 mm). First, the total height is measured as $H_a$ which includes all materials in the ultracentrifuge tube. Second, the height of the benefit layer is measured as $H_b$. Third, the structured surfactant layer is measured as $H_c$. The benefit layer is determined by its low moisture content (less than 10% water as measured by Karl Fischer Titration). It generally presents at the top of the centrifuge tube. The total surfactant layer height ($H_s$) can be calculated by this equation:

$$H_s = H_a - H_b$$

The structured surfactant layer components may comprise several layers or a single layer. Upon ultracentrifugation, there is generally an isotropic layer at the bottom or next to the bottom of the ultracentrifuge tube. This clear isotropic layer typically represents the non-structured micellar surfactant layer. The layers above the isotropic phase generally comprise higher surfactant concentration with higher ordered structures (such as liquid crystals). These structured layers are sometimes opaque to naked eyes, or translucent, or clear. There is generally a distinct phase boundary between the structured layer and the non-structured isotropic layer. The physical nature of the structured surfactant layers can be determined through microscopy under polarized light. The structured surfactant layers typically exhibit distinctive texture under polarized light. Another method for characterizing the structured surfactant layer is to use X-ray diffraction technique. Structured surfactant layer display multiple lines that are often associated primarily with the long spacings of the liquid crystal structure.

Finally, the structured domain volume ratio is calculated based on the following equation:

Structured Domain Volume Ratio=$H_c/H_s*100\%$

If there is no benefit phase present, use the total height as the surfactant layer height, $H_s=H_a$.

Method of Use

The mild multi-phase personal care compositions of the present invention are preferably applied topically to the desired area of the skin or hair in an amount sufficient to provide effective delivery of the skin cleansing agent, hydrophobic material, and particles to the applied surface. The compositions can be applied directly to the skin or indirectly via the use of a cleansing puff, washcloth, sponge or other implement. The compositions are preferably diluted with water prior to, during, or after topical application, and then subsequently the skin or hair rinsed or wiped off, preferably rinsed off of the applied surface using water or a water-insoluble substrate in combination with water.

The present invention is therefore also directed to methods of cleansing the skin through the above-described application of the compositions of the present invention. The methods of the present invention are also directed to a method of providing effective delivery of the desired skin active agent, and the resulting benefits from such effective delivery as described herein, to the applied surface through the above-described application of the compositions of the present invention.

Method of Manufacture

The mild multi-phase personal care compositions may be prepared by any known or otherwise effective technique, suitable for making and formulating the desired mild multi-phase product form. It is effective to combine toothpaste-tube filling technology with a spinning stage design. Additionally, the present invention can be prepared by the method and apparatus as disclosed in U.S. Pat. No. 6,213,166. The method and apparatus allows two or more compositions to be filled with a spiral configuration into a single container. The method requires that at least two nozzles be employed to fill the container. The container is placed on a static mixer and spun as the composition is introduced into the container.

Alternatively, it is effective to combine at least two phases by first placing the separate compositions in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. Specific non-limiting examples of such methods as they are applied to specific embodiments of the present invention are described in the following examples.

If the mild multi-phase personal care compositions comprise patterns of varying colors it can be desirable to package these compositions in a transparent or translucent package such that the consumer can view the pattern through the package. Because of the viscosity of the subject compositions it may also be desirable to include instructions to the consumer to store the package upside down, on its cap to facilitate dispensing.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and claims, are by weight and all numerical limits are used with the normal degree of accuracy afforded by the art, unless otherwise specified.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Each of the examples below are of mild multi-phase personal care compositions comprising 50%, by weight of the personal care composition, of a first phase and 50%, by weight of the mild multi-phase personal care composition, of a second phase. The amount of each component in a particular phase is provided as a weight percent based on the weight of the particular phase that contains the component.

Examples 1-7

The following examples described are non-limiting examples of mild multi-phase compositions.

|  | Ex. 1 | Ex. 2 | Ex. 3 | Ex. 4 |
|---|---|---|---|---|
| First Phase | Chemical | Chemical | Chemical | Chemical |
| CTFA Name | % w/w | % w/w | % w/w | % w/w |
| Water Distilled | 67.88 | 67.88 | 67.88 | 67.88 |
| Guar hydroxypropyl-trimonium chloride | 0.70 | 0.70 | 0.70 | 0.70 |
| Citric Acid Anhydrous USP | 1.00 | 1.00 | 1.00 | 1.00 |
| Glycerin | 0.30 | 0.30 | 0.30 | 0.30 |
| PEG 90M | 0.10 | 0.10 | 0.10 | 0.10 |
| Citric Acid Anhydrous USP | 0.09 | 0.09 | 0.09 | 0.09 |
| Hampene NA2 (Dissolvine NA-2X) | 0.06 | 0.06 | 0.06 | 0.06 |
| Sodium Trideceth Sulfate | 13.00 | 13.00 | 13.00 | 13.00 |
| Sodium Lauroamphoacetate | 9.20 | 9.20 | 9.20 | 9.20 |
| Steareth-2 | 1.80 | 0.00 | 0.00 | 0.00 |
| Sorbitan Monostearate | 0.00 | 1.80 | 0.00 | 0.00 |
| Glyceryl Monohydroxystearate | 0.00 | 0.00 | 0.00 | 1.80 |
| Peg-2 Stearate (Diethylene Glycol Stearate) | 0.00 | 0.00 | 0.00 | 0.00 |
| Glyceryl Monostearate | 0.00 | 0.00 | 0.00 | 0.00 |
| Laureth-2 | 0.00 | 0.00 | 0.00 | 0.00 |
| Propylene Glycol Stearate | 0.00 | 0.00 | 1.80 | 0.00 |

| | -continued | | | |
|---|---|---|---|---|
| Sodium Chloride | 3.50 | 3.50 | 3.50 | 3.50 |
| Perfume | 2.00 | 2.00 | 2.00 | 2.00 |
| DMDM Hydantoin | 0.37 | 0.37 | 0.37 | 0.37 |
| | 100.000 | 100.000 | 100.000 | 100.000 |
| Second Phase | | | | |
| Petrolatum | 60.00 | 60.00 | 60.00 | 60.00 |
| Mineral Oil | 40.00 | 40.00 | 40.00 | 40.00 |
| | 100.00 | 100.00 | 100.00 | 100.00 |
| Yield Point | 4.6 | 2.4 | 2 | 2 |
| Structured Domain Volume Ratio | 79% | 74% | 79% | 81% |
| Total Lather Volume | 1610 | 1870 | 2070 | 1630 |

| | Ex. 5 | Ex. 6 | Ex. 7 |
|---|---|---|---|
| First Phase | Chemical | Chemical | Chemical |
| CTFA Name | % w/w | % w/w | % w/w |
| Water Distilled | 67.88 | 67.88 | 67.88 |
| Guar hydroxypropyl-trimonium chloride | 0.70 | 0.70 | 0.70 |
| Citric Acid Anhydrous USP | 1.00 | 1.00 | 1.00 |
| Glycerin | 0.30 | 0.30 | 0.30 |
| PEG 90M | 0.10 | 0.10 | 0.10 |
| Citric Acid Anhydrous USP | 0.09 | 0.09 | 0.09 |
| Hampene NA2 (Dissolvine NA-2X) | 0.06 | 0.06 | 0.06 |
| Sodium Trideceth Sulfate | 13.00 | 13.00 | 13.00 |
| Sodium Lauroamphoacetate | 9.20 | 9.20 | 9.20 |
| Steareth-2 | 0.00 | 0.00 | 0.00 |
| Sorbitan Monostearate | 0.00 | 0.00 | 0.00 |
| Glyceryl Monohydroxy-stearate | 0.00 | 0.00 | 0.00 |
| Peg-2 Stearate (Diethylene Glycol Stearate) | 1.80 | 0.00 | 0.00 |
| Glyceryl Monostearate | 0.00 | 1.80 | 0.00 |
| Laureth-2 | 0.00 | 0.00 | 1.80 |
| Propylene Glycol Stearate | 0.00 | 0.00 | 0.00 |
| Sodium Chloride | 3.50 | 3.50 | 3.50 |
| Perfume | 2.00 | 2.00 | 2.00 |
| DMDM Hydantoin | 0.37 | 0.37 | 0.37 |
| | 100.000 | 100.000 | 100.000 |
| Second Phase | | | |
| Petrolatum | 60.00 | 60.00 | 60.00 |
| Mineral Oil | 40.00 | 40.00 | 40.00 |
| | 100.00 | 100.00 | 100.00 |
| Yield Point | 2.8 | 1.8 | 3.5 |
| Structured Domain Volume Ratio | 67% | 78% | 78% |
| Total Lather Volume | 1540 | 1790 | 2090 |

The compositions described above can be prepared by conventional formulation and mixing techniques. Prepare the first phase composition by first adding citric acid into water at 1:3 ratio to form a citric acid premix. Then, add the following ingredients into the main mixing vessel in the following sequence: water, sodium trideceth sulfate, sodium lauroamphoacetate, Steareth-2, sodium chloride, sodium benzoate, Disodium EDTA, glydant. Heat to 65-70° C. Start agitation of the main mixing vessel. In a separate mixing vessel, disperse polymers (Polyquaterium 10, Jaguar C-17, or N-Hance 3196) in water at 1:10 ratio and form a polymer premix. Add the completely dispersed polymer premix into the main mixing vessel with continuous agitation. Disperse Polyox WSR 301 in water and then add to the main mixing vessel. Then, add the rest of the water. Cool to 48° C. and add perfume into the batch. Keep agitation until a homogenous solution forms.

The second phase can be prepared by adding petrolatum into a mixing vessel. Heat the vessel to 190° F. (88° C.). Then, add mineral oil and particles. High shear the batch to ensure good particle dispersion. Keep agitating the batch and slowly cool down the batch to ambient temperature.

These phases can be combined by first placing the separate phases in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. The products remain stable at ambient for at least 180 days.

Examples 8-9

The following examples described are non-limiting examples of a mild body wash comprising a multi-phase personal care composition and particulate.

| | Ex. 8 | Ex. 9 |
|---|---|---|
| First Phase | Chemical | Chemical |
| CTFA Name | % w/w | % w/w |
| Water Distilled | 67.88 | 67.88 |
| Guar hydroxypropyl-trimonium chloride | 0.70 | 0.70 |
| Citric Acid Anhydrous USP | 1.00 | 1.00 |
| Glycerin | 0.30 | 0.30 |
| PEG 90M | 0.10 | 0.10 |
| Citric Acid Anhydrous USP | 0.09 | 0.09 |
| Hampene NA2 (Dissolvine NA-2X) | 0.06 | 0.06 |
| Sodium Trideceth Sulfate | 13.00 | 13.00 |
| Sodium Lauroamphoacetate | 9.20 | 9.20 |
| Steareth-2 (HLB = 4.9) | 1.80 | 1.80 |
| Sodium Chloride | 3.50 | 3.50 |
| Perfume | 2.00 | 2.00 |
| DMDM Hydantoin | 0.37 | 0.37 |
| | 100.000 | 100.000 |
| Second Phase | | |
| CTFA Name | % w/w | % w/w |
| Water Distilled | 66.38 | 66.38 |
| Guar hydroxypropyl-trimonium chloride | 0.70 | 0.70 |
| Citric Acid Anhydrous USP | 1.00 | 1.00 |
| Glycerin | 0.30 | 0.30 |
| PEG 90M | 0.10 | 0.10 |
| Citric Acid Anhydrous USP | 0.09 | 0.09 |

-continued

|  | Ex. 8 | Ex. 9 |
|---|---|---|
| Hampene NA2 (Dissolvine NA-2X) | 0.06 | 0.06 |
| Sodium Trideceth Sulfate | 13.00 | 13.00 |
| Sodium Lauroamphoacetate | 9.20 | 9.20 |
| Laureth-2 (HLB = 9.5) | 1.80 | 1.80 |
| Sodium Chloride | 3.50 | 3.50 |
| Perfume | 2.00 | 2.00 |
| DMDM Hydantoin | 0.37 | 0.37 |
| Polyethylene beads | 1.50 | 0 |
| Mica | 0 | 1.50 |
|  | 100.00 | 100.00 |

The compositions described above can be prepared by conventional formulation and mixing techniques. Prepare the first phase composition by first adding citric acid into water at 1:3 ratio to form a citric acid premix. Then, add the following ingredients into the main mixing vessel in the following sequence: water, sodium trideceth sulfate, sodium lauroamphoacetate, Steareth-2, sodium chloride, sodium benzoate, Disodium EDTA, glydant. Heat to 65-70° C. Start agitation of the main mixing vessel. In a separate mixing vessel, disperse polymers (Polyquaterium 10, Jaguar C-17, or N-Hance 3196) in water at 1:10 ratio and form a polymer premix. Add the completely dispersed polymer premix into the main mixing vessel with continuous agitation. Disperse Polyox WSR 301 in water and then add to the main mixing vessel. Then, add the rest of the water. Cool to 48° C. and add perfume into the batch. Keep agitation until a homogenous solution forms.

The second phase can be prepared similarly by conventional formulation and mixing techniques. Prepare by first adding citric acid into water at 1:3 ratio to form a citric acid premix. Then, add the following ingredients into the main mixing vessel in the following sequence: water, sodium trideceth sulfate, sodium lauroamphoacetate, Laureth-2, sodium chloride, sodium benzoate, Disodium EDTA, glydant. Heat to 65-70° C. Start agitation of the main mixing vessel. In a separate mixing vessel, disperse polymers (Polyquaterium 10, Jaguar C-17, or N-Hance 3196) in water at 1:10 ratio and form a polymer premix. Add the completely dispersed polymer premix into the main mixing vessel with continuous agitation. Disperse Polyox WSR 301 in water and then add to the main mixing vessel. Then, add the rest of the water. Cool to 48° C. and add perfume into the batch. Finally, add the particulate matter and keep agitation until a homogenous solution forms.

These phases can be combined by first placing the separate phases in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. The products remain stable at ambient for at least 180 days.

The following comparative examples versus the mild-multi-phased personal care composition described in the present application demonstrate the superior performance the composition of the present invention delivers.

Comparative Example 1

A body wash is procured having the following ingredients: water, sunflower seed oil, sodium laureth sulfate, sodium lauroamphoacetate, glycerin, petrolatum, lauric acid, cocamide MEA, fragrance, guar hydroxypropyltrimoniumchloride, lanolin alcohol, citric acid, DMDM hydantoin, tetrasodium EDTA, etidronic acid, titanium dioxide, PEG-30 dipolyhydroxystearate. The body wash is marketed under the trade name Dove™ All Day Moisturizing Body Wash by Lever Bros. Co., Greenwich Conn., USA. The body wash contains a Structured Domain Volume Ratio of at least about 42% and has a Total Lather Volume of 1410 ml, and a Flash Lather Volume of 310 ml, and a Yield Stress of 7 Pa.

Comparative Example 2

A body wash is procured having the following ingredients: water, petrolatum, ammonium laureth sulfate, sodium lauroamphoacetate, ammonium lauryl sulfate, lauric acid, fragrance, trihydroxystearin, citric acid, guar hydroxypropyl trimonium chloride, sodium benzoate, DMDM hydantoin, disodium EDTA, PEG-14M. The body wash is marketed under the trade name Oil of Olay® Daily Renewal Moisturizing Body Wash by Procter & Gamble, Inc., Cincinnati, Ohio, USA. The body wash contains a Structured Domain Volume Ratio of at least about 64% and has a Total Lather Volume of 1630 ml, a Flash Lather Volume of 410 ml, and a Yield Stress of 2.8 Pa.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A personal care article comprising a package containing a mild, multi-phase personal care composition comprising:
   a. a visually distinct cleansing phase comprising a surfactant component comprising:
      i. a branched anionic surfactant;
   b. a separate, visually distinct anhydrous benefit phase comprising at least about 50%, by weight of said benefit phase, of hydrophobic component having a Vaughan Solubility Parameter of about 5 to about 15 $(cal/cm^3)^{1/2}$;
      wherein said visually distinct cleansing phase and said visually distinct benefit phase are in physical contact within said package and are operable to remain separate, visually distinct phases;
      wherein said composition has a Structured Domain Volume Ratio of at least about 45%; and
      wherein said composition comprises a viscosity of about 10,000 centipoise or greater.
2. The personal care article of claim 1, wherein said composition has a Structured Domain Volume Ratio of at least about 60%.

3. The personal care article of claim 1, wherein said composition has a Structured Domain Volume Ratio of at least about 80%.

4. The personal care article of claim 1, wherein said surfactant component provides a Total Lather Volume of at least about 600 ml.

5. The personal care article of claim 1, wherein said surfactant component provides a Total Lather Volume of at least about 800 ml.

6. The personal care article of claim 1, wherein said surfactant component provides a Yield Point of greater than about 0.2 Pascal.

7. The personal care article of claim 1, wherein said surfactant component comprises surfactants selected from the group consisting of anionic surfactant, nonionic surfactant, amphoteric surfactant, and mixtures thereof.

8. The personal care article of claim 1, wherein said composition further comprising a particle; wherein said particle is selected from the group consisting of natural, synthetic, semi-synthetic, hybrid, and combinations thereof.

9. The personal care article of claim 1, wherein the branched anionic surfactant is sodium trideceth sulfate.

10. The personal care article of claim 1, wherein the visually distinct cleaning phase comprises an isotropic phase and a liquid crystal phase.

11. A personal care article comprising a package containing a mild multi-phase personal care composition comprising:
  a. a visually distinct cleansing phase comprising a surfactant component, wherein the surfactant component comprises an anionic surfactant, a nonionic surfactant, and an amphoteric surfactant;
  b. a visually distinct anhydrous benefit phase comprising at least about 50%, by weight of said benefit phase, of hydrophobic component, wherein said hydrophobic component comprises petrolatum;
    wherein said visually distinct cleansing phase and said visually distinct benefit phase are in physical contact within said package;
    wherein said composition has a Structured Domain Volume Ratio of at least about 45%;
    wherein said composition comprises a viscosity of about 10,000 centipoise or greater.

12. The personal care article of claim 11, wherein said anionic surfactants comprises sodium trideceth sulfate.

13. The personal care article of claim 11, wherein said surfactant component comprises a plurality of anionic surfactants, and wherein said plurality of anionic surfactants comprises sodium trideceth sulfate and sodium lauryl sulfate.

14. The personal care article of claim 11, wherein said nonionic surfactant comprises polyhydroxy fatty acid amides.

15. The personal care article of claim 11, wherein said amphoteric surfactant comprises sodium lauroamphoacetate.

16. The personal care article of claim 11, wherein said composition has a Structured Domain Volume Ratio of at least about 80%.

17. The personal care article of claim 11, wherein said surfactant component provides a Total Lather Volume of at least about 800 ml.

18. A personal care article comprising a package containing a mild multi-phase personal care composition comprising:
  a. a visually distinct cleansing phase comprising a surfactant component, wherein the surfactant component comprises an anionic surfactant, a nonionic surfactant, and an amphoteric surfactant, wherein said anionic surfactant comprises sodium trideceth sulfate;
  b. a visually distinct anhydrous benefit phase comprising at least about 50%, by weight of said benefit phase, of hydrophobic component, wherein said hydrophobic component comprises petrolatum;
    wherein said visually distinct cleansing phase and said visually distinct benefit phase are in physical contact within said package; and
    wherein said composition has a Structured Domain Volume Ratio of at least about 45%; and
    wherein said composition comprises a viscosity of about 10,000 centipoise or greater.

19. The personal care article of claim 18, wherein said surfactant component comprises a plurality of anionic surfactants, and wherein said plurality of anionic surfactants comprises sodium trideceth sulfate and sodium lauryl sulfate.

20. The personal care article of claim 18, wherein said nonionic surfactant comprises polyhydroxy fatty acid amides.

21. The personal care article of claim 18, wherein said amphoteric surfactant comprises sodium lauroamphoacetate.

22. The personal care article of claim 18, wherein said composition has a Structured Domain Volume Ratio of at least about 60%.

23. The personal care article of claim 18, wherein said surfactant component provides a Total Lather Volume of at least about 600 ml.

24. The personal care article of claim 1, wherein said benefit phase is substantially free of surfactant.

25. The personal care article of claim 1, wherein said benefit phase comprises zero percent, by weight, of water.

26. The personal care article of claim 11, wherein said benefit phase is substantially free of surfactant.

27. The personal care article of claim 11, wherein said benefit phase comprises zero percent, by weight, of water.

28. The personal care article of claim 18, wherein said benefit phase is substantially free of surfactant.

29. The personal care article of claim 18, wherein said benefit phase comprises zero percent, by weight, of water.

* * * * *